United States Patent
Farmer et al.

(10) Patent No.: US 11,549,067 B2
(45) Date of Patent: Jan. 10, 2023

(54) REMEDIATION OF RAG LAYER AND OTHER DISPOSABLE LAYERS IN OIL TANKS AND STORAGE EQUIPMENT

(71) Applicant: Locus Solutions IPCo, LLC, Solon, OH (US)

(72) Inventors: Sean Farmer, North Miami Beach, FL (US); Ken Alibek, Solon, OH (US); Kent Adams, Oro Valley, AZ (US); Karthik N. Karathur, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 309 days.

(21) Appl. No.: 16/617,208

(22) PCT Filed: Jun. 12, 2018

(86) PCT No.: PCT/US2018/037054
§ 371 (c)(1),
(2) Date: Nov. 26, 2019

(87) PCT Pub. No.: WO2018/231791
PCT Pub. Date: Dec. 20, 2018

(65) Prior Publication Data
US 2021/0130704 A1    May 6, 2021

Related U.S. Application Data

(60) Provisional application No. 62/518,217, filed on Jun. 12, 2017.

(51) Int. Cl.
*E21B 43/26* (2006.01)
*C10G 32/00* (2006.01)
(Continued)

(52) U.S. Cl.
CPC .......... *C10G 32/00* (2013.01); *B01D 17/047* (2013.01); *C02F 1/50* (2013.01); *C02F 3/347* (2013.01);
(Continued)

(58) Field of Classification Search
CPC .. E21B 43/26; C09K 8/58; C09K 8/66; C09K 8/84
(Continued)

(56) References Cited

U.S. PATENT DOCUMENTS 3,871,956 A    3/1975   Azarowics
4,450,908 A    5/1984   Hitzman
(Continued)

FOREIGN PATENT DOCUMENTS

CN    103449696 A    12/2013
CN    104109646 A    10/2014
(Continued)

OTHER PUBLICATIONS

Amani, H., et al., "Comparative study of biosurfactant producing bacteria in MEOR applications." Journal of Petroleum Science and Engineering. 2010, 75:209-214.
(Continued)

*Primary Examiner* — William D Hutton, Jr.
*Assistant Examiner* — Ashish K Varma
(74) *Attorney, Agent, or Firm* — Saliwanchik, Lloyd & Eisenschenk

(57) ABSTRACT

The subject invention provides microbe-based products, as well as their use to improve oil production and refining efficiency by, for example, remediating the disposable layers in oil tanks and other oil storage units. In preferred embodiments, the microbe-based products comprise biochemical-producing yeast and growth by-products thereof, such as, e.g., biosurfactants. The subject invention can be used to
(Continued)

remediate rag layer and/or other dissolved solid layers that form in water-oil emulsions. Furthermore, the subject invention can be used for remediating solid impurities, such as sand, scale, rust and clay, in produced water, flow-back, brine, and/or fracking fluids.

9 Claims, 1 Drawing Sheet

(51) Int. Cl.
| B01D 17/04 | (2006.01) |
| C02F 1/50 | (2006.01) |
| C02F 3/34 | (2006.01) |
| C09K 8/58 | (2006.01) |
| C09K 8/66 | (2006.01) |
| C09K 8/84 | (2006.01) |
| C10G 33/04 | (2006.01) |
| C12N 1/16 | (2006.01) |
| C12P 19/44 | (2006.01) |
| C02F 101/32 | (2006.01) |
| C02F 103/10 | (2006.01) |

(52) U.S. Cl.
CPC .............. *C09K 8/58* (2013.01); *C09K 8/66* (2013.01); *C09K 8/84* (2013.01); *C10G 33/04* (2013.01); *C12N 1/16* (2013.01); *C12P 19/44* (2013.01); *E21B 43/26* (2013.01); *C02F 2101/32* (2013.01); *C02F 2103/10* (2013.01); *C02F 2303/22* (2013.01); *C02F 2305/04* (2013.01); *C10G 2300/1033* (2013.01); *C10G 2300/208* (2013.01)

(58) Field of Classification Search
USPC ....................................... 166/308.1
See application file for complete search history.

(56) References Cited

U.S. PATENT DOCUMENTS

| 4,511,730 | A | * | 4/1985 | Fields .................. C09K 8/584 560/33 |
| 4,522,261 | A | | 6/1985 | McInerney et al. |
| 5,165,477 | A | | 11/1992 | Shell et al. |
| 5,364,474 | A | | 11/1994 | Williford, Jr. |
| 6,033,901 | A | | 3/2000 | Powell, Jr. |
| 7,556,654 | B1 | | 7/2009 | Nero |
| 7,681,638 | B2 | | 3/2010 | Soni et al. |
| 9,441,115 | B2 | | 9/2016 | Wu et al. |
| 9,550,937 | B2 | | 1/2017 | Campbell et al. |
| 9,683,164 | B2 | | 6/2017 | Gunawan et al. |
| 9,884,986 | B2 | | 2/2018 | Gunawan et al. |
| 10,023,787 | B2 | | 7/2018 | Benoit et al. |
| 10,190,038 | B2 | | 1/2019 | Armstrong et al. |
| 2002/0143071 | A1 | | 10/2002 | Gutnick et al. |
| 2009/0029879 | A1 | | 1/2009 | Soni et al. |
| 2010/0044031 | A1 | | 2/2010 | Fallon et al. |
| 2011/0027838 | A1 | * | 2/2011 | Harding ................ C12N 1/205 435/101 |
| 2011/0139262 | A1 | | 6/2011 | Aburto Anell et al. |
| 2012/0122740 | A1 | | 5/2012 | Roldan Carrillo et al. |
| 2013/0062053 | A1 | | 3/2013 | Kohr et al. |
| 2013/0324406 | A1 | | 12/2013 | Chisholm et al. |
| 2014/0273150 | A1 | | 9/2014 | Angel |
| 2014/0305649 | A1 | | 10/2014 | Tang et al. |
| 2014/0332212 | A1 | | 11/2014 | Ayers et al. |
| 2014/0360727 | A1 | | 12/2014 | Milam et al. |
| 2015/0037302 | A1 | | 2/2015 | Bralkowski et al. |
| 2015/0045290 | A1 | | 2/2015 | Coutte et al. |
| 2015/0068950 | A1 | | 3/2015 | See et al. |
| 2015/0259642 | A1 | | 9/2015 | Sangwai et al. |
| 2015/0300139 | A1 | * | 10/2015 | Armstrong .............. E21B 43/26 166/278 |
| 2016/0145487 | A1 | | 5/2016 | Alam et al. |
| 2016/0160111 | A1 | | 6/2016 | Smith et al. |
| 2016/0222280 | A1 | | 8/2016 | Kohr et al. |
| 2016/0244347 | A1 | | 8/2016 | Angel |
| 2017/0044586 | A1 | * | 2/2017 | Duran .................... C12P 19/44 |

FOREIGN PATENT DOCUMENTS

| CN | 105567580 A | 5/2016 |
| CN | 105753283 A | 7/2016 |
| WO | 2007129332 A1 | 11/2007 |
| WO | 2011008570 A2 | 1/2011 |
| WO | 2014152350 A1 | 9/2014 |
| WO | 2015167864 A1 | 11/2015 |
| WO | 2017044953 A1 | 3/2017 |
| WO | 2018049182 A2 | 3/2018 |
| WO | 2018107162 A1 | 6/2018 |

OTHER PUBLICATIONS

Bach, H., et al., "An Exocellular Protein from the Oil-Degrading Microbe Acinetobacter venetianus RAG-1 Enhances the Emulsifying Activity of the Polymeric Bioemulsifier Emulsan." Applied and Environmental Microbiology, May 2003, 69(5): 2608-2615.

Castaneda, L.C., et al., "Current situation of emerging technologies for upgrading of heavy oils." Catalysis Today, 2014, 220-222: 248-273.

De Almeida, D., et al., "Biosurfactants: Promising Molecules for Petroleum Biotechnology Advances." Frontiers in Microbiology, Oct. 2016, 7(1718): 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Elshafie, A. E., et al., "Sophorolipids Production by Candida bombicola ATCC 22214 and its Potential Application in Microbial Enhanced Oil Recovery." Frontiers in Microbiology, Nov. 2015, 6(1324): 1-11.

El-Sheshtawy, H.S., et al., "Production of biosurfactants by Bacillus licheniformis and Candida albicans for application in microbial enhanced oil recovery." Egyptian Journal of Petroleum, 2016, 25: 293-298.

Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.

Kurtzman, C.P., et al., "Production of sophorolipid biosurfactants by multiple species of the Starmerella (*Candida*) bombicolayeast clade." FEMS Microbiol Lett, 2010, 311: 140-146.

Nitschke, M., et al., "Production and properties of a surfactant obtained from Bacillus subtilis grown on cassava wastewater." Bioresource Technology, 2006, 97: 336-341.

Nur, H.A., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.

Pacwa-Plociniczak, M. et al., "Review: Environmental Applications of Biosurfactants: Recent Advances." Int. J. Mol. Sci., 2011, 12: 633-654.

Rocha E Silva, F.C.P., et al., "Yeasts and bacterial biosurfactants as demulsifiers for petroleum derivative in seawater emulsions." AMB Expr., 2007, 7(202): 1-13.

Santos, D.K.F., et al., "Biosurfactants: Multifunctional Biomolecules of the 21st Century." International Journal of Molecular Sciences, 2016, 17(401): 1-31.

Sen, R., "Biosurfactants: Advances in Experimental Medicine and Biology." Landes Bioscience and Springer Science +Business Media, LLC, 2010, 672: 1-331.

(56) References Cited

OTHER PUBLICATIONS

Sharma, A. et al., "A study on biosurfactant production in *Lactobacillus* and *Bacillus* sp." Int. J. Curr. Microbiol. App. Sci., 2014, 3(11):723-733.
Silva, R., et al., "Applications of Biosurfactants in the Petroleum Industry and the Remediation of Oil Spills." International Journal of Molecular Sciences, 2014, 15: 12523-12542.
Thaniyavarn, J., et al., "Production of Sophorolipid Biosurfactant by Pichia anomala." Bioscience, Biotechnology, and Biochemistry, 2008, 72(8): 2061-2068.

\* cited by examiner

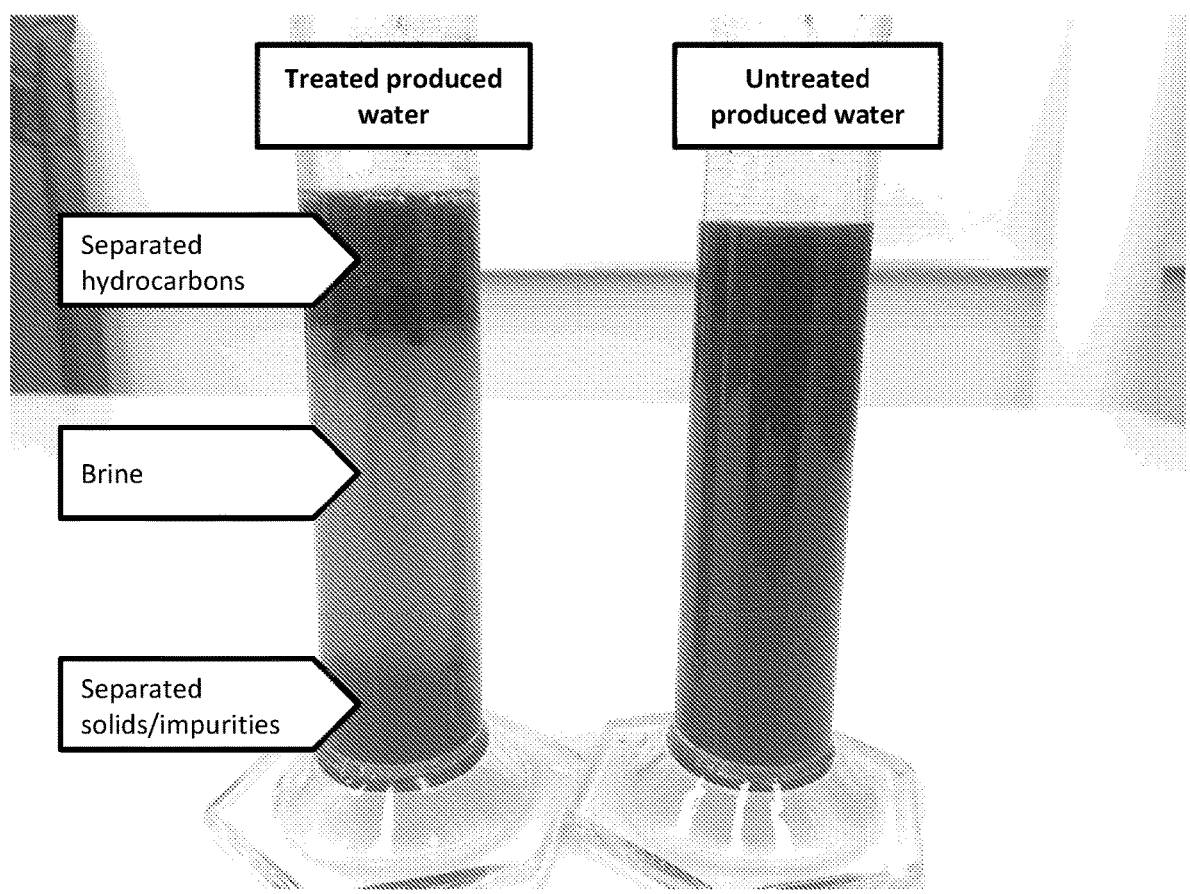

REMEDIATION OF RAG LAYER AND OTHER DISPOSABLE LAYERS IN OIL TANKS AND STORAGE EQUIPMENT

CROSS-REFERENCE TO RELATED APPLICATION

This application is a National Stage Application of International Application No. PCT/US2018/037054, filed Jun. 12, 2018; which claims the benefit of U.S. provisional patent application Ser. No. 62/518,217, filed Jun. 12, 2017, which is incorporated herein by reference in its entirety.

BACKGROUND OF THE INVENTION

Crude petroleum contains impurities, including water, salts, and solid particulate matter or sediment, that may corrode and/or build up solid deposits in, for example, refinery units. Additionally, oil storage tanks inevitably take in water due to venting and leakage, or through entrained water in the crude oil product itself. Water and other impurities must be removed from the crude oil before it can be processed in a refinery.

Prior to refining, impurities can be removed from crude oil by a process known as "desalting," where hot crude oil is mixed with water and a suitable agent to form a water-in-oil emulsion. The water-in-oil emulsion provides contact between the oil and water so that the salts pass into solution in the water. Another process for reducing the basic sediment and water of crude oil is known as dehydration, which uses, for example, mechanical separation and/or chemical demulsifiers.

Various oil recovery and refining operations generate both oil/water and water/oil emulsions, which are present in drainage water, spills, separator skimmings, tank bottoms and oil recovery traps. Water-in-oil emulsions are viscous, concentrated substances formed when oil comes into contact with water and solids. Metal particles and other solids may be coated with surfactants in such a manner that they are preferentially wetted by the oil rather than the water. When agitation occurs, the water becomes dispersed in the oil as a fine emulsion, and these small water droplets, together with the oil-coated solids, maintain the stability of the emulsion.

The tendency of heavy oils to contain water-in-oil emulsions can be attributed to the presence of certain hydrocarbon molecules found in heavy crudes. Particularly, asphaltenes and high naphthenic acids in heavy crudes tend to form stable, water-in-oil emulsions. The polar naphthenic acids and asphaltenes, along with sub-micron size solids, such as silica, clay, and other minerals, undesirably stabilize heavy crude petroleum emulsions.

During desalting, emulsions are passed into a high voltage electrostatic field inside a closed separator vessel. The electrostatic field coalesces and breaks the emulsion into an oil continuous phase and a water continuous phase. The oil continuous phase rises to the top of the solution to form the upper layer in the desalter. From there, the oil phase is continuously drawn off while the water continuous phase (or "brine") sinks to the bottom and is continuously removed therefrom. In addition, solids present in the crude will accumulate in the bottom of the desalter vessel, sometimes in the form of a sandy sludge layer.

During operation of desalting units, an emulsion phase of variable composition and thickness often forms at the oil-water interface. This emulsion phase may become stable and persist in the desalting vessel. If this emulsion phase (commonly known as the "rag layer") does stabilize and become too thick, the oil continuous phase will contain too much brine and the lower brine phase will contain unacceptable amounts of oil.

In extreme cases, this can result in the emulsion being withdrawn from the top or bottom of the unit. Oil entrainment in the water phase is a serious problem, as it is expensive to remedy outside the unit. When an excessive stable emulsion layer builds up, it becomes necessary to withdraw the rag layer and process it for reintroduction into the refinery.

Emulsion layers are best kept at a consistent amount in the separator in order to maximize the separation capacity and reduce the contamination of the outgoing oil and water. For example, if the emulsion layer becomes too thick, excessive electrical loading, erratic voltage readings, or carryover of water into the oil or loss of oil into the water layer may result.

Traditional remedies include adding chemical emulsion breakers, reducing processing rates, shutting down the desalter to remove the emulsion and increasing the size of the separator tank. Shutdown or reduction of feed rate is uneconomical, while the use of chemical demulsifiers may cause problems in downstream catalytic units sensitive to deactivation by the chemicals. Thus, formation of a stable emulsion rag layer can be detrimental when it leads to early shutdown of the desalting processes and disruption of refinery operation, deactivation of catalysts, and the fouling and/or plugging of process equipment.

In some cases, processes for the separation of water from heavy oil, or dehydration, result in an emulsion rag layer as well. Further processing of the rag layer can be useful to recover the crude oil and discharge the water. Some methods of processing crude oil fluids comprising water and oil emulsions employ the use of mechanical separators and/or gravitation. However, if a thick rag layer has formed in the crude oil fluids, the use of storage tanks and mechanical separators may become difficult and expensive. This is particularly true with emulsions of heavy oil and water produced from a reservoir formation, as such crude oil fluids can contain as much as about 60% water by volume.

Chemical separation methods are also known for dehydrating crude oil. Dehydration chemicals, or demulsifiers, counteract emulsifying agents, allowing the dispersed droplets of the emulsion to coalesce into larger droplets and settle out of the matrix. However, the effectiveness of demulsifiers on heavy crude oils, particularly those containing asphaltenes, naphthenic acids and inorganic solids, can be limited, and supplemental methods of dehydration may be required.

Efficient production of oil depends upon the proper functioning of equipment and the ability of processing operations to extract the maximum amount of usable hydrocarbons from crude oil fluids. Thus, there is a continuing need for effective separation of water, impurities and solid particles from crude oil in areas such as oil production, storage, transportation, and refining. Even further needed are simple, cost-effective methods of removing the rag layer from oil storage tanks and vessels.

BRIEF SUMMARY OF THE INVENTION

The subject invention provides microbes, as well as by-products of their growth, such as biosurfactants and/or other metabolites, as well as methods of using these microbes and their by-products. Advantageously, the microbe-based products and methods of the subject invention are non-toxic, environmentally-friendly, operational-friendly and cost-effective.

In one embodiment, the subject invention provides microbe-based products, as well as methods of their use, to improve oil production by, for example, remediating disposable layers and/or phases in water-oil emulsions. Specifically, the subject invention can be used to rapidly demulsify entrained hydrocarbons in water-oil emulsions, and to destabilize solid impurities from brine fluids.

Advantageously, the compositions and methods of the subject invention can decrease the cost of mechanical remediation of disposable layers and/or phases (e.g., rag layer, brine and solid impurities), aid in the recovery of more pure hydrocarbons from crude fluids, and provide safer means of disposing of and/or reusing water and other fluids used and/or produced in oil and gas operations.

In certain embodiments, the subject invention provides microbe-based compositions for improved oil production efficiency, wherein the compositions comprise one or more biochemical-producing microorganisms and/or by-products of their growth. In preferred embodiments, the microorganisms are yeasts.

In a specific embodiment, the microbes are biosurfactant-producing yeasts. The invention provides, for example, a microbe-based product comprising cultivated *Starmerella* clade yeasts and/or growth by-products thereof, cultivated *Wickerhamomyces* or *Pichia* clade yeasts, and/or growth by-products thereof, or any yeast species related to these clades (e.g., belonging to the same family or genus), and/or growth by-products thereof. In some embodiments, the microbe-based product can be used in conjunction with other chemical, mechanical, thermal and/or microbial treatments.

In certain embodiments, the microbe-based composition of the subject invention comprises biosurfactants. The biosurfactants can be produced in situ by the microorganisms of the subject composition, and/or the biosurfactants can be produced separately by any biosurfactant-producing microorganism and added in a crude and/or purified form. In some embodiments, the composition further comprises an ionic or semi-ionic liquid.

The compositions of the subject invention can further comprise natural or chemical inhibitors of bacterial growth to prevent excessive growth of undesirable microorganisms, e.g., sulfur-reducing bacteria, in the treatment environment. For example, biosurfactants, acids (e.g., lactic acid, acetic acid or citric acid), and/or antibiotics can be included in the composition for such purposes.

The compositions of the subject invention can have advantages over, for example, biosurfactants alone, due to the use of the entire microbial culture, either with or without living cells. These advantages can include one or more of the following: high concentrations of mannoprotein as a part of a yeast cell wall's outer surface; the presence of beta-glucan in yeast cell walls; and the presence of biosurfactants, solvents, and/or other metabolites (e.g., lactic acid, ethyl acetate, ethanol, etc.) in the culture.

In one embodiment, the subject invention provides methods of producing a microbial growth by-product by cultivating a microbe strain of the subject invention under conditions appropriate for growth and production of the by-product. In one embodiment, the microbe-based combinations are obtained through cultivation processes ranging from small to large scale. The cultivation process can be, for example, submerged cultivation, solid state fermentation (SSF), and/or a combination thereof. Optionally, the microbial growth by-product can further be purified, although in some embodiments, the growth by-product is utilized in a crude form, e.g., without being separated from the fermentation broth in which it is produced. Examples of growth by-products include, but are not limited to, biosurfactants, enzymes, proteins, and other metabolites.

In one embodiment, the cultivation of microbial growth by-products comprises separating the growth by-products from the microorganisms. This produces large amounts of unused biomass, comprising living or inactive cells. This biomass can be useful as a demulsification agent in any setting where water-oil or oil-water emulsions exist, such as, for example, rag layer remediation, sewage treatment, slaughterhouses and paper mills.

In certain embodiments, the subject invention provides a method for improving oil production efficiency, wherein the method comprises applying a composition of the subject invention to crude oil fluids having a water-oil emulsion therein, and mixing the composition and the crude oil fluids continuously until the water-oil emulsion demulsifies into a water phase and a hydrocarbon phase. The composition can be added pre-mixed to the crude oil fluids, or, the individual components can be added separately and mixed in the crude oil fluids.

In one embodiment, the method can also be used to remediate disposable layers, such as rag layer and/or sludge layer, present in a storage unit having crude fluids therein.

Advantageously, the methods operate by demulsifying entrained hydrocarbons in water-oil emulsions, and/or by destabilizing, and separating out, solid impurities, such as clay, scale and sand, from brine fluids. Thus, oil production efficiency can be improved, as hydrocarbons can be separated from crude fluids and sent to refineries more quickly, with minimal additional processing.

In one embodiment, mixing can be performed using any device or method known in the art. For example, mixing can be accomplished by pumping air into the storage unit, or using an agitator. In one embodiment, the mixing is performed continuously until demulsification of the water-oil emulsion occurs, i.e., the water-oil emulsion has separated into its various phases, and/or until solid impurities have separated out.

In one embodiment, the method can be used for treating produced water, flow-back, brine and/or fracking fluids having dissolved solids, hydrocarbons and/or other impurities therein, wherein a composition of the subject invention is applied to the produced water, flow-back, brine and/or fracking fluids. As used herein, "treating" refers to remediation or removal of the dissolved solids and/or other impurities from the produced water, flow-back, brine and/or frac water.

In certain embodiments, the water/brine fluids have been extracted from a water-oil emulsion that was present in crude fluids treated according to the subject methods.

Optionally, the method further comprises mixing the composition with the water, flow-back, brine and/or fracking fluids continuously until the dissolved solids, hydrocarbons and/or other impurities separate from the water, flow-back, brine and/or fracking fluids. Examples of impurities that can separate and/or settle from the fluids include, e.g., clay, scale, sand, dissolved solids, and/or paraffins.

The water, flow-back, brine and/or frac water, can then be safely disposed of, for example, into injection wells. In one embodiment, the water/brine fluids can be recycled after treatment and reused rather than discarded.

The compositions and methods of the subject invention can demulsify entrained hydrocarbons in water-oil emulsions. In one embodiment, the methods can further comprise extracting oil or other hydrocarbons from the crude fluids after the water-oil emulsion has sufficiently separated into its various phases. The compositions and methods of the subject invention can also separate out solids and impurities entrained in crude oil fluids (including produced water/brine fluids). After removal of the hydrocarbons and water, any leftover solid impurities can be removed using, for example, a shovel, and disposed of by any means known in the industry.

Application of the microbe-based compositions can be performed during production, transportation, storage, and/or refining of crude oil. For example, the subject products can be applied to crude fluids in a storage tank located at any stage of the production and/or refining process. The subject products can also be applied, for example, to crude fluids that are undergoing, or that have already undergone, dehydration and/or desalting. Furthermore, the subject compositions can be applied to crude fluids present in a dehydration or desalting vessel, or in a separator vessel.

BRIEF DESCRIPTION OF THE FIGURES

FIG. 1 shows vials containing produced water treated with a composition according to the subject invention, versus untreated water. The treatment vial exhibits distinct, separated layers of hydrocarbon, brine, and solids after 3 hours.

DETAILED DESCRIPTION

The subject invention provides advantageous microbe-based products that contain microbes and/or their growth by-products. The by-products of their growth can include, for example, biosurfactants, solvents, and/or enzymes. The subject invention also provides methods of using these microbe-based products. Advantageously, the microbe-based products and methods of the subject invention are non-toxic, environmentally-friendly, operational-friendly and cost-effective.

In one embodiment, the subject invention provides microbe-based products, as well as their use, to improve oil production by, for example, remediating disposable layers in water-oil emulsions. Specifically, the subject invention can be used to rapidly demulsify entrained hydrocarbons in water-oil emulsions, as well as destabilize and separate out solid impurities, e.g., clay, scale, sand, dissolved solids, and/or paraffins, from water and brine fluids. This allows for efficient removal of impurities, as well as more efficient recovery of more pure hydrocarbons from the crude fluids that require less processing during refining. Thus, crude oil production yields and efficiency can be improved.

In certain embodiments, the subject invention provides a method for improving oil production efficiency by applying to crude oil fluids having a water-oil emulsion therein, a composition comprising microbes and/or products of their growth. In one embodiment, the method can also be used to remove rag layer and/or sludge layer present in a storage unit having crude fluids therein, wherein a composition of the subject invention is applied to the storage unit, and optionally, mixed with the crude fluids.

In one embodiment, the methods can further comprise mixing the crude fluids and composition using any device or method known in the art. Mixing is preferably performed continuously until demulsification of the water-oil emulsion occurs, i.e., the water-oil emulsion has separated into its various phases, or until solid impurities have separated out.

In one embodiment, the method can be used to remove dissolved solids and/or other impurities from produced water, flow-back, brine and/or frac water, wherein a composition of the subject invention is applied to the water, flow-back, brine and/or frac water. Optionally, the method further comprises mixing the composition and the water/brine continuously until the solids and/or impurities separate out. The water, flow-back, brine and/or frac water, can be safely disposed of, for example, into injection wells. In one embodiment, the water/brine can be recycled after treatment and reused rather than discarded.

The compositions and methods of the subject invention can demulsify entrained hydrocarbons in water-oil emulsions. In one embodiment, the methods can further comprise extracting oil or other hydrocarbons from the crude fluids after the water-oil emulsion has sufficiently separated into its various phases. The compositions and methods of the subject invention can also separate out solids and impurities entrained in crude oil fluids (including produced water/brine fluids). After removal of the hydrocarbons and water, any leftover solid impurities can be removed using, for example, a shovel, and disposed of by any means known in the industry.

Selected Definitions

When water is produced with oil it is frequently in the form of an emulsion. As used herein, an "emulsion" is a heterogeneous liquid system consisting of two immiscible liquids, with one of the liquids being intimately dispersed in the form of droplets in the second liquid. The matrix of an emulsion is called the external or continuous phase, while the portion of the emulsion that is in the form of small droplets is called the internal, dispersed, or discontinuous phase. In most emulsions of crude oil and water, the water is finely and spherically dispersed in the oil. This is referred to as a "water-in-oil emulsion." The spherical form of the water droplets is a result of interfacial tension (IFT), which forces the water to present a minimum surface area to the oil. As used herein, water-in-oil emulsions can further comprise "crude oil fluids" and "crude fluids."

As used herein, "impurity" or "contaminant" or refers to any substance that causes another substance or object to become fouled, contaminated or impure. Impurities can be living or non-living and can be inorganic or organic substances, particles or deposits. Impurities can include, but are not limited to, hydrocarbons, such as asphaltenes, tar and bitumen; fats, oils and greases (FOG), such as cooking grease and lard; lipids; waxes, such as paraffin; resins; biofilms; or any other substances referred to as, for example, dirt, dust, sludge, crud, slag, grime, scum, plaque, buildup, or residue. Rag layer and sludge layer can also be included in the phrase "impurity." The phrase "solid impurities" includes particles of, for example, sand, scale, silt, rust, clay and other dissolved solids.

As used herein, "rag layer" refers to an intermediate emulsion phase present at the oil and water interface in water-oil emulsions. The rag layer can comprise dispersed oil, water droplets, fine solids, minerals, organic matter, and other impurities, with the total amount and composition of the rag layer varying greatly between different oil tanks depending on the source of the crude oil.

As used herein, "sludge layer" refers to a phase in crude fluids, usually present at the bottom of oil storage tanks, comprising heavy hydrocarbons, such as paraffins, and other impurities such as sand, rust and heavy metals. Similar to a rag layer, the composition of a sludge layer can vary greatly between different oil tanks depending on the source of the crude oil.

As used herein, "storage unit" refers to any container or vessel used, or suitable for use, in holding liquids, such as crude oil, crude fluids, brine, water, or other fluids, particularly those fluids associated with oil and gas production. Storage units can include storage tanks, dehydration vessels, desalting vessels and separators, and can be stationary or portable (e.g., associated with a tanker truck).

As used herein, "remediating" as used in the context of rag layer, sludge layer, and other impurities means removal or reduction of those impurities from crude oil. Remediating can include demulsifying, separating, purifying, defouling, decontaminating, clearing, cleaning and/or unclogging. Remediating can further include controlling, inhibiting or preventing further formation of rag, sludge, or emulsion of water and oil from occurring.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The by-products of growth may be, for example, metabolites (e.g., biosurfactants), cell membrane components, expressed proteins, and/or other cellular components.

The microbes may be live or inactive, in a vegetative state, in spore form, in mycelial form, in any other form of propagule, or a mixture of these. The microbes may be planktonic or in a biofilm form, or a mixture of both. The microbes may be intact or lysed. The cells may be absent, or present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more cells or propagules per milliliter of the composition. As used herein, a propagule is any portion of a microorganism from which a new and/or mature organism can develop, including but not limited to, cells, conidia, cysts, spores (e.g., reproductive spores, endospores and exospores), mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, carriers (e.g., water, salt solutions, or any other appropriate carrier), added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

A "metabolite" refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

As used herein, an "isolated" or "purified" nucleic acid molecule, polynucleotide, polypeptide, protein or organic compound, such as a small molecule, is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of other molecules, or the amino acids that flank it, in its naturally-occurring state. A purified or isolated microbial strain means that the strain is removed from the environment in which it exists in nature. Thus, the isolated strain may exist as, for example, a biologically pure culture, or as spores (or other forms of the strain) in association with, e.g., a carrier.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduces" means a negative alteration of at least 1%, 5%, 1°%, 25%, 50%, 75%, or 100%.

As used herein, "reference" means a standard or control condition.

As used herein, "salt-tolerant" in the context of a microbe means the microbe is capable of growing in a sodium chloride concentration of fifteen (15) percent or greater. In a specific embodiment, "salt-tolerant" refers to the ability to grow in 150 g/L or more of NaCl.

As used herein, "surfactant" means a surface-active compound that lowers the surface tension (or interfacial tension) between two liquids or between a liquid and a solid. Surfactants act as, e.g., detergents, wetting agents, emulsifiers, foaming agents, and/or dispersants. A "biosurfactant" is a surface-active substance produced by a living cell.

As used herein, "heavy oil" or "heavy hydrocarbons" mean viscous hydrocarbon fluids. Heavy hydrocarbons may include highly viscous hydrocarbon fluids such as heavy oil, extra heavy oil, tar, tar sands, fuel oil and/or asphalt. Heavy and extra heavy oils are highly viscous with a density close to or even exceeding water. Heavy hydrocarbons may comprise moderate to high quantities of paraffins, resins and asphaltenes, as well as smaller concentrations of sulfur, oxygen, and nitrogen. Heavy hydrocarbons may also include aromatics or other complex ring hydrocarbons. Additional elements may also be present in heavy hydrocarbons in trace amounts. Heavy hydrocarbons may be classified by API gravity. Heavy hydrocarbons generally have an API gravity below about 20°. Heavy oil, for example, generally has an API gravity of about 10-20°, whereas extra heavy oil generally has an API gravity below about 12°. The viscosity of heavy hydrocarbons is generally greater than about 200 cp at reservoir conditions, and that of extra heavy oil is generally about 10,000 cp or more.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Compositions for Improved Oil Production Efficiency

In certain embodiments, the subject invention provides microbe-based compositions for improved oil production efficiency, wherein the compositions comprise one or more biochemical-producing microorganisms and/or by-products of their growth. In certain embodiments, the composition further comprises an ionic or semi-ionic liquid. Optionally, the composition can also comprise nutrients for microbial growth, including, for example, sources of carbon, nitrogen, magnesium, phosphorous, micronutrients and proteins, as well as bacterial growth inhibitors, such as acids and/or antibiotics.

The microorganisms useful according to the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microbes are biosurfactant-producing producing microorganisms. Even more preferably, the microorganism is a yeast or fungus. Yeast and fungus species suitable for use according to the current invention, include without limitation, for example, *Aspergillus*, *Aureobasidium* (e.g., *A. pullulans*), *Blakeslea*, *Candida* (e.g., *C. bombicola* or *C. apicola*) *Entomophthora*, *Issatchenkia*, *Kluyveromyces*, *Mortierella*, *Mycorrhiza*, *Phycomyces*, *Phythium*, *Pichia*, *Pseudozyma* (e.g., *P. aphidis*), *Rhizopus*, *Saccharomyces* (e.g., *S. cerevisiae*, *S. boulardii sequela* or *S. torula*), *Starmerella* (e.g., *S. bombicola*), *Thraustochytrium*, and/or *Wickerhamomyces* (e.g., *W. anomalus*).

In one embodiment, the microorganism is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Such yeasts can include, but are not limited to, *Candida*, *Cryptococcus*, *Debaryomyces* (e.g., *D. hansenii*), *Hanseniaspora* (e.g., *H. uvarum*), *Hansenula*, *Kluyveromyces*, *Pichia* (e.g., *P. anomala*, *P. guielliermondii*, *P. occidentalis*, or *P. kudriavzevii*), *Saccharomyces*, *Torulopsis*, *Ustilago* (e.g., *U. maydis*), *Wickerhamomyces* (e.g., *W. anomalus*), *Williopsis*, *Zygosaccharomyces* (e.g., *Z. bailii*), and others.

In one embodiment, the microbe is a cultivated killer yeast strain, or a mutant thereof, such as a *Wickerhamomyces* clade yeast or a *Pichia* clade yeast, or any other yeast related thereto by family or genus. Exemplary yeasts include *W. anomalus* (*Pichia anomala*), *P. guielliermondii*, *P. occidentalis*, and/or *P. kudriavevii*. In particular, *W. anomalus* is an effective producer of sophorolipids, ethyl acetate, and other metabolites, such as solvents, enzymes and toxins.

In one embodiment, the microbe is cultivated *Starmerella* clade yeast, or a mutant thereof. *S. bombicola*, for example, is an effective produce of sophorolipid biosurfactants.

Other microbial strains in addition to those described above, including others belonging to the same family or genus as those described above, and, for example, other fungal or yeast strains capable of accumulating significant amounts of, for example, emulsifiers, biosurfactants and/or solvents (e.g., mannoprotein, beta-glucan, ethanol, lactic acid and other metabolites that have, for example, bio-emulsifying and surface/interfacial tension-reducing properties) can be used in accordance with the subject invention.

In one embodiment, the subject invention provides a yeast fermentation product. The yeast fermentation product can comprise simply the fermentation broth containing the yeast and/or the metabolites produced by the yeast and/or any residual nutrients. The product of fermentation may be used directly without extraction or purification. If desired, extraction and purification can be easily achieved using standard extraction and/or purification methods or techniques described in the literature.

The yeasts in the yeast fermentation product may be in an active or inactive form. The yeast-based products may be used without further stabilization, preservation, and storage. Advantageously, direct usage of these yeast-based products preserves a high viability of the microorganisms, reduces the possibility of contamination from foreign agents and undesirable microorganisms, and maintains the activity of the by-products of microbial growth.

The yeasts and/or broth resulting from their growth can be removed from the vessel in which they are grown and transferred to an oil storage tank for immediate use.

The composition may further comprise a bacterial growth inhibiting compound, such as, for example, an antibiotic (e.g., streptomycin, ampicillin or erythromycin), lactic acid, acetic acid, citric acid, or others known in the art, which help inhibit growth of undesirable bacteria, such as sulfur-reducing bacteria. In one embodiment, the yeast of the composition produces biochemicals, such as killer toxins, which can help to this end. In one embodiment, the biosurfactants of the subject composition can also help control undesirable bacterial growth.

In certain embodiments, the microbe-based composition of the subject invention comprises, a the microbial growth by-product, one or more biosurfactants. The biosurfactants can be produced in situ by the microorganisms of the subject composition, and/or the biosurfactants can be produced by other microorganisms and added to the composition in a crude and/or purified form. For example, a crude form biosurfactant may comprise fermentation broth in which it was produced.

Biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes. In one embodiment, the microbial biosurfactant is a glycolipid such as rhamnolipids (RLP), sophorolipids (SLP), trehalose lipid (TL) or mannosylerythritol lipid (MEL). In one embodiment, the microbial biosurfactant is a lipopeptide, such as a surfactin, iturin, fengycin or lichenysin. Combinations of any of these biosurfactants are also envisioned.

In certain embodiments, the concentration of the one or more biosurfactants in the composition is 0.01 to 90 by weight % (wt %), preferably 0.1 to 50 wt %, and more preferably 0.1 to 20 wt %.

In one embodiment, the one or more biosurfactants are selected from glycolipid biosurfactants. Preferably, the glycolipid is a sophorolipid. In specific embodiments, the glycolipid is present in the composition at about 0.01 g/L to about 20.0 g/L, about 0.5 g/L to about 10.0 g/L, preferably from about 2.0 to about 5.0 g/L.

In certain embodiments, the biosurfactants work synergistically with solvents and other metabolites that are in the composition and/or produced by the microbes.

In some embodiments, ionic or semi-ionic liquids can be added to the composition to increase its effectiveness. Ionic liquids can act as co-solvents and can prevent the formation of ring bonds in hydrocarbon compositions, which is one cause of hydrocarbon precipitation.

Ionic liquids are composed entirely of ions or a combination of cations and anions. Many ionic liquids are in the form of organic salts with melting points below 100° C., or often even lower than room temperature. The most common ionic liquids are those prepared from organic-based cations and inorganic or organic anions. At least one ion has a delocalized charge and one component is organic, which prevents the formation of a stable crystal lattice. Ionic liquids may be suitable, for example, for use as catalysts and solvents in alkylation and polymerization reactions, as well as in dimerization, oligomerization acetylation, metatheses and copolymerization reactions. Properties of ionic liquids, such as melting point, viscosity and solubility are determined by the substituents on the organic component and by the counter-ion.

Exemplary ionic liquids according to the subject composition include, but are not limited to, ethyl ammonium nitrate or glycerin/magnesium sulfate heptahydrate. Preferably, the concentration of ionic liquid in the composition ranges from about 0.1% to about 5% (by volume), or about 0.5%, 1%, 2%, 3%, 4%, or any value therebetween.

In certain embodiments, the compositions of the subject invention have advantages over, for example, biosurfactants alone, due to, for example, the use of the yeast fermentation product. These advantages include one or more of the following: high concentrations of mannoprotein as a part of a yeast cell wall's outer surface; the presence of beta-glucan in yeast cell walls; the presence of biosurfactants in the culture; and the presence of solvents and other metabolites (e.g., lactic acid, ethanol, ethyl acetate, etc.) in the culture. These advantages are present when using active or inactive yeast.

Other suitable additives that may be added to the composition include substances that are customarily used for such preparations. Example of such additives include non-biological surfactants, emulsifying agents, lubricants, buffering agents, solubility controlling agents, pH adjusting agents, preservatives, stabilizers and ultra-violet light resistant agents.

In one embodiment, the composition may further comprise buffering agents, including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt as polyprotic acid such as sodium bicarbonate or carbonate, sodium sulfate, sodium phosphate, sodium biphosphate, can be included in the formulation.

Other suitable additives can include, for example, terpenes, terpene alcohols, C8-C14 alcohol ester blends, glycols, glycol ethers, acid esters, diacid esters, petroleum hydrocarbons, amino acids, alkanolamines, and amines, preferably, methyl or isobutyl esters of C4-C6 aliphatic dibasic esters and n-methyl-2 pyrolidone.

Examples of terpenes include D-limonene and α and β pinene and terpene alcohols, including a terpineol. C8-C14 alcohol ester blends include EXXATE 900, 1000, 1200 from Exxon Chemical; glycols include propylene glycol, dipropylene glycol, and triproplylene glycol; and glycol ethers include dipropylene glycol monomethyl ether, propylene glycol monomethyl ether, propylene glycol-n-butyl ether, ethylene glycol monobutyl ether, and diethylene glycol monobutyl ether. Acid esters include methyl oleate and methyl linoleate, and diacid esters include methyl or butyl diesters of glutaric, adipic, and succinic acids. Petroleum hydrocarbons include AROMATIC 100, AROMATIC 150 ISOPAR M, and ISOPAR K.

Amines such as morpholine; 1,3-dimethyl-2-imidazolidinone; 1,3-propanediamine; 2-amino-1,3-propanediol; and 3-amino propanol; as well as alkanolamines such as triethanolamine, diethanolamine, 2-aminomethyl propanol, and monoethanolamine act as dispersants for contaminants and solubilize fatty acids and oils. Amino acids, provide non-toxic alternatives to monoethanolamine, and act as metal chelators. Methyl or isobutylesters of C4-C6 aliphatic dibasic esters and n-methyl-2 pyrolidone are also useful.

Other additives typically used in cleaning compositions may be used, including water softening agents, sequesterants, corrosion inhibitors, and antioxidants, which are added in amounts effective to perform their intended function. These additives and amounts thereof are well within the skill of the art.

Suitable water softening agents include linear phosphates, styrene-maleic acid co-polymers, and polyacrylates. Suitable sequesterants include 1,3-dimethyl-2-immidazolidinone; 1-phenyl-3-isoheptyl-1,3-propanedione; and 2 hydroxy-5-nonylacetophenoneoxime. Examples of corrosion inhibitors include 2-aminomethyl propanol, diethylethanolamine benzotraizole, and methyl benzotriazole. Antioxidants include, for example, (BHT) 2,6-di-tert-butyl-para-cresol, (BHA) 2,6-di-tert-butyl-para-anisole, Eastman inhibitor O A BM-oxalyl bis (benzylidenehydrazide), and Eastman DTBMA 2,5-di-tert-butylhydroquinone.

In some embodiments, diluents can be added to the composition to aid sludge removal and, for example, reducing the viscosity of oil produced from the subject methods. Diluents can include, for example, naphthas, gas condensates, light crude oil, synthetic crude oil, gasoline, kerosene, MTBE, TAME, DME, alcohols (e.g., ethyl alcohol), ethane, propane, heptane, toluene and butanone, All additives should have a flash point greater than 100° F., preferably greater than 150° F. and more preferably 195° F. TCC to achieve a final product flash point greater than 200° F.

Use of Microbe-Based Products in Oil Production

In certain embodiments, the subject invention provides a method for improving oil production efficiency by demulsifying entrained hydrocarbons in water-oil emulsions, and by destabilizing, and separating out, solid impurities, such as clay, scale and sand, from brine fluids. Advantageously, the methods allow for greater efficiency and productivity when producing oil, as more pure hydrocarbons can be separated from crude fluids and refined more efficiently, e.g., with minimal additional processing. Furthermore, the methods can be useful for processing of light to heavy crude oils, as well as for crude oil that is undergoing, or has undergone, dehydration and/or desalting.

In specific embodiments, the subject invention provides a method for improving oil production efficiency, wherein the method comprises applying a composition comprising microbes and/or growth by-products thereof, to crude oil fluids having a water-oil emulsion therein; and mixing the composition and the crude oil fluids continuously until the water-oil emulsion demulsifies into a water phase and a hydrocarbon phase. In one embodiment, the method can also be used to remediate disposable layers, such as rag layer and/or sludge layer, present in a storage unit having crude fluids therein The microbe-based products utilized according to the subject methods can reduce the interfacial tension of water and oil, thus releasing impurities trapped in crude oil and other fluids, and allowing the various phases therein to separate from one another. For example, the subject invention can be used to separate, e.g., water, oil, sands, scales, dissolved solids, and/or paraffins in crude fluids in as little as 2 to 3 hours, after which the impurities can then be removed and, for example, taken to landfill.

In preferred embodiments, the composition is applied to crude fluids present in an oil storage tank, desalting vessel, dehydration vessel and/or a refining separator. As used herein, "applying" a composition or product refers to contacting it with a target or site such that the composition or product can have an effect on that target or site. The effect can be due to, for example, microbial growth and/or the action of a biosurfactant, solvent and/or other compound. For example, a composition can be applied to crude oil fluids by being injected, poured or pumped into a storage unit having the crude oil fluids therein. Furthermore, the components of the composition can be pre-mixed and applied in one application, or the components can be added separately or in stages to the crude oil fluids and mixed therein.

During application of the subject compositions to crude oil fluids, a basic initial dosage of the composition can be, but is not limited to, 5 gallons to 2,000 gallons of composition, or 10 gallons to 1,000 gallons, or from 20 to 500 gallons. For maintenance purposes, at least about 5 gallons of composition can be applied to, for example, a storage unit on a periodic basis, e.g. biweekly, monthly, bimonthly.

When the crude oil fluids comprise disposable layers, such as rag layer and/or sludge layer, the composition of the subject invention is preferably applied in an amount (e.g., volume) equal to or greater than the amount of rag layer and/or sludge present. For example, the ratio of amount of rag layer to amount of composition can be 1:1, 1:2, 1:3, 1:4, 1:5, or greater.

When enough fluid is present, the method can comprise mixing (or circulating) the crude fluids and the composition using any device or method known in the art. For example, mixing can be accomplished by pumping air into a storage unit, or using an agitator. In one embodiment, the mixing is performed continuously until demulsification of the water-oil emulsion occurs, i.e., the water-oil emulsion has separated into its various phases. In another embodiment, mixing occurs until solid impurities, e.g., clay, scale, sand, dissolved solids, and/or paraffins, have separated and/or settled from crude fluids.

For example, mixing can occur continuously for, e.g., 1 to 96 hours, or 24 to 72 hours, preferably 48 to 72 hours. Additionally, prior to circulating, the composition may be allowed to sit, for example, 8 to 24 hours.

The sitting time, mixing time and dosage depend on the amount of disposable phases and/or impurities that are present or anticipated to be present in the crude fluids, as well as the depth and size of the unit.

In one embodiment, the method further comprises extracting oil or other hydrocarbons from the crude fluids after the water-oil emulsion has sufficiently separated into its various phases. In another embodiment, the water and/or brine phase can be extracted and recycled, for example, as frac fluid in fracking wells. After removal of the hydrocarbons and water from the storage unit, any leftover solid impurities in the unit can be removed mechanically or by hand, e.g., using a shovel.

In preferred embodiments, the composition according to the subject methods comprises biochemical-producing microbes. Even more preferably the microbes are yeasts, selected from *Starmerella* clade yeasts, *Wickerhamomyces* clade yeasts, *Pichia* clade yeasts, and/or any yeast that is closely-related thereto (e.g., belonging to the same genus or family). The yeasts can be active or inactive when applied to the crude oil fluids.

Optionally, the method can further comprise adding one or more crude form or purified biosurfactants; an ionic or semi-ionic liquid; nutrients that are beneficial to microbial growth, such as, for example, nitrogen, nitrate, phosphorus, magnesium and/or carbon; and/or one or more bacterial growth inhibitors, to the storage unit. In one embodiment, the method comprises applying a microbe-based composition as described previously in embodiments of the subject description.

In one embodiment, the biosurfactant can be, for example, a glycolipid (e.g., sophorolipid, rhamnolipid, trehalose lipid, mannosylerythritol lipid) and/or a lipopeptide (e.g., surfactin, iturin, fengycin, lichenysin). In preferred embodiments, the biosurfactant is a glycolipid, even more preferably, a sophorolipid.

In one embodiment, the subject invention provides efficient methods of removing dissolved solids and/or other impurities from produced water, flow-back, brine and/or frac fluids.

In one embodiment, the method comprises applying the subject microbe-based products to the produced water, flow-back, brine and/or fracking fluids; and mixing the composition with the water, flow-back, brine and/or fracking fluids continuously until dissolved solids and/or impurities separate and/or settle therefrom. The dissolved solids and/or impurities can then be removed.

In one embodiment, the method can further comprise recovering any hydrocarbons that separate from the produced water, flow-back, brine and/or fracking fluids, thus enhancing the amount of oil recovered from the fluids.

In one embodiment, the method comprises disposing of the water, flow-back, brine and/or frac fluids (after the impurities have been removed and hydrocarbons have been recovered) by injecting the water, flow-back, brine and/or frac fluids into an injection well. Advantageously, disposal in this manner is safer with treatment than without treatment due to the reduction or elimination of impurities that could potentially cause, for example, groundwater contamination.

Alternatively, in one embodiment, the method further comprises recycling the water, flow-back, brine and/or frac fluids rather than disposing of it. The recycled fluids can be reused in the operations of a fracking well, in water flooding, or for other uses, such as in agriculture.

As an example, in fracking operations, the constituents in the water used to fracture wells can include chemical additives as well as sand or other solid particles that are carried to the rock fractures. The frac fluid can pick up other contaminants while in a rock formation as well, including but not limited to, barium, calcium bicarbonate, iron, magnesium sulfate, sodium chloride, and strontium. A large percentage of the injected frac fluid will then return to the surface, with much of the remaining water eventually making its way into the well bore during production. That fluid is then transported to saltwater disposal wells for reinjection into a porous rock formation. The ability to treat and subsequently recycle water reduces or eliminates the expense of hauling the wastewater away for disposal, as well as reduces or eliminates the amount of water consumed by a fracking or other well operation.

In one embodiment, methods are provided for treating, for example, borehole, oilfield, transportation, transmission, and/or oil refinery equipment. In certain embodiments, the methods are used to improve oil production, as well as maintenance of, for example, pipes, drills, tanks, separators and other structures and equipment involved in oil and/or gas production, transportation, storage and/or refining. The subject invention can be useful for applications including, but not limited to, aspects of horizontal well, vertical well, and/or fracking well operations.

The application of the microbe-based compositions can be performed during production, transportation, storage, and/or refining of crude oil. For example, the subject products can be applied to crude fluids in a storage tank located at any staged of the production and/or refining process. The subject products can also be applied, for example, to crude fluids that are undergoing, or that have already undergone, dehydration and/or desalting. Furthermore, the subject compositions can be applied to crude fluids present in a dehydration or desalting vessel, or in a separator vessel.

The gas and oil processing equipment that can be remediated according to the subject invention includes all types and varieties of equipment associated with gas and oil recovery, transmission, transportation and processing where water-in-oil emulsions might occur, and particularly, where rag layer and/or sludge accumulates. This includes, for example, gas and oil well casings, pumps, rods, pipes, lines, tanks, dehydrators, desalters, separators, and the like. It is contemplated that the present composition may be used with all such equipment.

In one embodiment, the compositions of the subject invention may be applied directly to equipment as a prophylactic measure. For example, prior to placing crude oil into a storage unit or separator, the composition can be poured into the unit, and/or the inner surfaces of the unit can be sprayed or coated with the composition to aid in the prevention of rag and sludge formation, or to increase the rate of demulsification and destabilization of impurities present in crude fluids that are later added to the unit.

The microbe-based product may be applied with a composition that promotes adherence of the microbe-based product to a surface to be treated. The adherence-promoting substance may be a component of the microbe-based product or it may be applied simultaneously with, or sequentially with, the microbe-based product. Adherence-promoters can include organic or inorganic particles, ions such as calcium, magnesium, phosphate, and sodium, iron, carbon sources that are metabolized to acetyl coenzyme A, acetyl phosphate, and acetate.

Growth of Microbes According to the Subject Invention

The subject invention provides methods for cultivation of microorganisms and production of microbial metabolites and/or other by-products of microbial growth. The fermentation processes utilized may be small to large scale, and can include, for example, submerged or surface fermentation, or combinations thereof. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

In one embodiment, the subject invention provides methods of producing a biosurfactant by cultivating a microbe strain of the subject invention under conditions appropriate for growth and surfactant production; and, optionally purifying the surfactant. In certain embodiments, the biosurfactant is used in a crude form, meaning it is left in the fermentation broth in which it was produced.

In one embodiment the subject invention also provides methods of producing enzymes, proteins and/or other microbial metabolites by cultivating a microbe strain of the subject invention under conditions appropriate for growth and production of the desired growth by-product; and, optionally, purifying the growth by-product.

Fermentation can be performed in any fermenter or cultivation reactor for industrial use. In one embodiment, the growth vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, canola oil, coconut oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention further provides a method for producing microbial metabolites such as ethanol, lactic acid, beta-glucan, proteins, peptides, metabolic intermediates, polyunsaturated fatty acid, and lipids. The metabolite content produced by the method can be, for example, at least 20%, 30%, 40%, 50%, 60%, 70%, 80%, or 90%.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of the microbial growth by-product.

The biomass content of the fermentation broth may be, for example from 5 g/l to 180 g/l or more. In one embodiment, the solids content of the broth is from 10 g/l to 150 g/l. In one embodiment, where the microbial growth by-product is concentrated, purified, and/or otherwise separated from the growth medium, a significant amount of cell biomass is leftover. These leftover cells can be active or inactive, and can be useful in either state. For example, the subject methods allow for use of active or inactive yeast cell biomass as demulsifying agents in any setting where water-oil or oil-water emulsions exist, for example, rag layer remediation, sewage treatment, paper manufacturing, and slaughterhouses.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

Advantageously, the microbe-based products can be produced in remote locations. In one embodiment, the microbe-based products can be used for human nutrition and/or disease prevention and/or treatment. The microbe growth facilities may operate off the grid by utilizing, for example, solar, wind and/or hydroelectric power.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., oil recovery, drilling, mining, waste treatment, etc.). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients, pH control agents, and defoaming agents), which makes the system efficient and eliminates the need to stabilize cells or separate them from their culture broth. Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization, have been sporulated or have sat in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the broth in which the microbes are grown. If desired, the compositions can have a high density of vegetative cells or a mixture of vegetative cells and reproductive spores.

Advantageously, the compositions can be tailored for use at a specified location. In one embodiment, the microbe growth facility is located on, or near, a site where the microbe-based products will be used.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve oil production, transmission and/or refining. Local microbes can be identified based on, for example, salt tolerance, ability to grow at high temperatures, and the use of genetic identification of the sequences described herein.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. It should be understood that the examples and embodiments described herein are for illustrative purposes only and that various modifications or changes in light thereof will be suggested to persons skilled in the art and are to be included within the spirit and purview of this application and the scope of the appended claims.

Example 1—Fermentation of *Starmerella bombicola* for Sophorolipid (Slp) Production in a 550 Gallon Reactor A portable, fully enclosed reactor, designed specifically for yeast growth and biosurfactant production, is operated by PLC and comprises water filtration, a temperature control unit, an impeller and a microsparger. The reactor has a working volume of 500 gallons when growing *S. bombicola* for SLP production.

In preferred embodiments, the nutrients for SLP production comprise glucose, urea, yeast extract, and used vegetable oil.

The reactor is inoculated with 50 liters of liquid culture grown in another reactor. The duration of the cultivation cycle for SLP production is 5 days, at 25° C. and pH 3.5. The final concentration of SLP is roughly 10-15% of working volume, containing 70-75 gallons of SLP.

The culture can be collected into a separate tank. After SLP is allowed to settle to the bottom of the tank, it can be removed and processed as desired. The remaining (approximately) 420 gallons of culture in the tank can comprise from 3-5 g/L of residual SLP, as well as leftover cell biomass.

Example 2—Fermentation of *Wickerhamomyces* and *Pichia* for Producing Cell Biomass A movable airlift reactor operated by PLC with water filtration, temperature control unit, and microsparger for sufficient aeration is used. The process can be carried out as batch cultivation process. The 800 gallon reactor is specifically designed for growing yeasts and has a working volume of 700 gallons when growing *Wickerhamomyces* or *Pichia* clade yeasts.

In preferred embodiments, the nutrients comprise glucose, urea, yeast extract, and used vegetable oil. Inoculation of this reactor requires up to 5% liquid seed culture of working volume. The duration of the cultivation cycle is 24-30 hours, at a temperature 25-30° C. and pH 3.5-4.5.

The final product comprises 25-30 gallons of liquid culture inoculum. Because of the short duration of fermentation, the final product does not contain biosurfactants. Sophorolipids can be added to the product at a concentration of about 1-3% or 1-1.5% if desired.

Example 3—Fermentation of *Pseudozyma APHIDIS* for Mannosylerythritol Lipid (MEL) Production in Portable 14 L Reactor This reactor is a steam autoclavable jacketed glass vessel with air spurge and Rushton impeller. It is equipped with DO, pH, temperature, and foam probe. It has an integrated control station with a color touchscreen interface, built-in pumps, gas flow controllers, and pH/DO foam/level controllers. The working volume of the reactor is 10 liters.

Nutrient medium composition: Sodium nitrate, Potassium phosphate, Magnesium sulfate, yeast extract, and vegetable oil. Inoculum can be a 1 to 2 day old culture of *Pseudozyma aphidis*, at about 5-10% of the total culture volume. Cultivation duration and sample collection occurs at 9-15 days. Final MEL production can reach 800-1000 grams, and leftover cell biomass can be used in active or inactivated form as, for example, a demulsifying agent.

Example 4—Treatment of Produced Water

The subject microbe-based product is applied to produced water from an oil well and allowed to sit for 3 hours. As shown in FIG. 1, the treated produced water separates into clearly defined phases, with hydrocarbons suspended on top of the brine layer, and solids/impurities settling at the bottom. The control sample of produced water left untreated remains in an emulsified state with no defined layers or separation.

We claim:

1. A method of dehydrating recovered heavy crude oil fluids comprising a water-oil emulsion and solid impurities, wherein the method comprises applying a composition comprising a yeast and/or a growth by-product thereof to the recovered heavy crude oil fluids, wherein said recovered heavy crude oil fluids are being stored in an oil storage tank, mixing the composition and the recovered heavy crude oil fluids in the oil storage tank until the water-oil emulsion demulsifies into a water phase and a hydrocarbon phase, and the solid impurities settle out of the crude oil fluids, and extracting the water phase and the solid impurities from the oil storage tank, wherein the yeast is *Starmerella bombicola* or *Wickerhamomyces anomalus* and wherein the growth by-product is a biosurfactant.

2. The method of claim 1, wherein mixing is performed using an air pump or an agitator.

3. The method of claim 1, used to remediate an amount of rag layer present in the recovered crude oil fluids.

4. The method of claim 3, wherein the composition is applied to the recovered crude oil fluids in an amount equal to or greater than the amount of rag layer in the recovered crude oil fluids.

5. The method of claim 1, wherein the biosurfactant is a glycolipid selected from sophorolipids, rhamnolipids, trehalose lipids and mannosylerythritol lipids.

6. The method of claim 1, wherein the biosurfactant is present in the composition at a concentration of 0.1% by weight to 90% by weight.

7. The method of claim 1, further comprising applying an ionic liquid at a concentration of 1% to 5% by volume to the recovered crude oil fluids.

8. The method of claim 7, wherein the ionic liquid is ethyl ammonium nitrate or glycerin/magnesium sulfate heptahydrate.

9. The method of claim 1, further comprising applying a bacterial growth inhibitor to the recovered crude oil fluids.

* * * * *